United States Patent

Wahlberg

[11] Patent Number: 5,520,654
[45] Date of Patent: May 28, 1996

[54] CATHETER DEVICE

[75] Inventor: Ulf H. Wahlberg, Helsingborg, Sweden

[73] Assignee: BOC Ohmeda AB, Helsingborg, Sweden

[21] Appl. No.: 156,338

[22] Filed: Nov. 22, 1993

[30] Foreign Application Priority Data

Nov. 26, 1992 [SE] Sweden .................................. 9203566

[51] Int. Cl.⁶ ................................................. A61M 5/178
[52] U.S. Cl. ........................... 604/164; 604/110; 604/198
[58] Field of Search ....................... 604/51–53, 158–172, 604/192, 198, 263, 110; 606/108

[56] References Cited

U.S. PATENT DOCUMENTS

| | | | |
|---|---|---|---|
| 4,850,961 | 7/1989 | Wanderer et al. | 604/53 |
| 4,917,669 | 4/1990 | Bonaldo | 604/164 |
| 4,950,252 | 8/1990 | Luther et al. | 604/164 |
| 4,957,488 | 9/1990 | Cameron et al. | 604/161 |
| 5,102,394 | 4/1992 | Lasaitis et al. | 604/263 |
| 5,154,699 | 10/1992 | Ryan | 604/198 |
| 5,171,231 | 12/1992 | Heiliger | 604/164 |
| 5,176,650 | 1/1993 | Haining | 604/164 |
| 5,176,655 | 1/1993 | McCormick et al. | 604/198 |
| 5,279,590 | 1/1994 | Sinko et al. | 604/263 |
| 5,279,591 | 1/1994 | Simon | 604/263 |
| 5,304,136 | 4/1994 | Erskine et al. | 604/110 |
| 5,312,359 | 5/1994 | Wallace | 604/164 |

Primary Examiner—John D. Yasko
Assistant Examiner—Ronald K. Stright, Jr.
Attorney, Agent, or Firm—Roger M. Rathbun; Larry R. Cassett

[57] ABSTRACT

A device comprises an elongate, tubular sheath (4) having an anterior and a posterior end (6; 8), a pointed needle (18) arranged in the sheath (4) for displacement between a first and a second end position, a catheter (26) initially supported by the needle (18), and an attachment for displacing the needle (18) between the first and the second end position. The novelty of the invention resides in that the sealing means for sealing the anterior, initially open end (6) of the sheath (4) is detachably connected to the attachment, that the sealing means further is detachably connected to the catheter (26), that the sealing means, during the displacement of the needle (18) from the first to the second end position, is moved towards the anterior end (6) of the sheath (4) to a sealing position, and that the sealing means is fixed in the sealing position for substantial sealing of the anterior end (6) of the sheath (4).

16 Claims, 5 Drawing Sheets

CATHETER DEVICE

BACKGROUND OF THE INVENTION

The present invention relates generally to infusion cannulae, and more specifically to devices for protecting a needle and the point of the needle, both before and after use of such infusion cannulae.

The existence of serious infectious diseases, such as AIDS and hepatitis, which may infect medical personnel through blood, other body fluids or tissue parts, makes the treatment and the care of patients extremely risky, as each patient is a potential source of infection.

After the discovery of HIV, a large number of people in the medical service, ambulance personnel, nurses, doctors and others, have been infected, e.g. by physical contact with or an inadvertent stick by an infected needle that has been used when treating blood-infected patients.

To protect medical personnel who are directly involved in the care of such highrisk patients, intense work has been done to develop syringes and infusion cannulae as well as protective means in such syringes and infusion cannulae to prevent physical contact with an infected needle and protect against inadvertent needle stick.

One example of such a device is described in U.S. Pat. No. 4,957,488, where a catheter is arranged inside a divided needle and where means is provided for preventing puncture of the catheter by unintentional forward displacement of the needle, once the withdrawal of the needle has been commenced. When the entire needle has been withdrawn, different components are detached, such as a part of an extension hose, which is quite unacceptable in view of the risk of infection.

Another example of a protective device of the abovementioned type is disclosed in U.S. Pat. No. 4,950,252. Use is here made of an elongate sheath cooperating with needle-protecting means. In an initial position, the needle and the catheter, supported by the needle, extend from one short side of the sheath. In conjunction with the withdrawal of the needle, said means is displaced relative to the sheath, and the used needle is thus retracted into the needle protecting means.

Yet another example of such a device is described in U.S. Pat. No. 4,917,669, where a needle-supporting means is arranged in an elongate sheath for longitudinal displacement therein. In an initial position, the needle is located within the sheath. By axial displacement of said means relative to the sheath, the needle and the catheter, supported by the needle, are extended from one short side of the sheath. When the catheter has been placed in the patient's vein, the procedure is reversed, i.e. the needle is retracted relative to the sheath so as finally to be enclosed thereby.

U.S. Pat. No. 4,850,961 describes a device which in this context must be considered to represent the closest prior art. Also in this device, the needle and the catheter, supported by the needle, are initially located inside an elongate sheath. In this case too, a needle-supporting means is operated to release the needle and the catheter by axial displacement of said means relative to the sheath. At the end of the reversed procedure, i.e. in conjunction with the withdrawal of the used needle, a lug, employed for displacing said means, enters a recess provided in the sheath and not accessible from outside, which means that the lug cannot be used again for extending the needle. This prior-art solution however suffers from a number of drawbacks. One is that the lug, employed for displacing the needle-supporting means, will be located, in the extended position of the needle, at a relatively great distance from the point of the needle. To guide the needle or control the movement of the point of the needle as accurately as possible, the device should however be gripped as far towards the anterior end as possible. Such anterior gripping is however not feasible, since the needle and the catheter supported by the needle would be retracted into the sheath if the grip about the lug is released. Another drawback of this device will be described below.

The known art thus provides different solutions for protecting medical personnel and others from used, possibly contaminated needles. However, all the known solutions suffer from more or less serious drawbacks. The loosening or detaching of parts after use of the needle, which is the case in the device disclosed in U.S. Pat. No. 4,957,488, is of course quite unacceptable. Also in the devices described in U.S. Pat. No. 4,917,669 and 4,850,961 there is considerable risk of unintentional or intentional exposure of the used needle.

In the device of U.S. Pat. No. 4,917,669, the needle is, after use, located in a sheath enclosing it. The short side of the sheath through which the needle and the catheter pass is however open, which is unsatisfactory, even if the point of the needle is located within the sheath and there is no imminent risk, in normal use of the device, of inadvertent contact with the needle point. The needle is locked in this end position by the same mechanism as is used for fixing the needle in the corresponding position prior to use of the device. In a preferred embodiment, this mechanism consists of a recess which is formed in an elongate slot provided in the sheath, and which comprises regions of the slot having a reduced width, the recess and said regions of reduced slot width cooperating with an operating member of the needle-supporting means, which passes through said slot. It will be appreciated that such a mechanism does not offer any adequate protection against renewed extension of the needle, especially since the locking mechanism can be damaged in connection with the use of the device. Moreover, a disadvantageous effect is that blood adhering to the needle after use may drip through the open short side in the sheath or through the slots formed in the sheath.

Attempts have been made to solve the problems discussed with reference to U.S. Pat. No. 4,917,669, by means of the device according to U.S. Pat. No. 4,850,961. As mentioned above, this device has an elongate slot in the sheath which encloses the needle both before and after use of the device. Through this slot passes a lug which is connected to a needle-supporting means and which is displaced relative to the sheath for extending and withdrawing the needle. After the needle has been used, the lug should be retracted so far as to enter a recess in the sheath, whereby it becomes inaccessible to the operator and thus cannot be displaced again. One problem in this context is that it is not practically possible without a tool, i.e. a pointed object, to move the lug as far rearwards as to reach the intended position. By using a catheter having a catheter housing of reduced dimensions, it has been possible to make smaller the opening in one short side of the sheath, through which pass the needle and the catheter supported thereby. Although this may be considered to be an advantage, this solution must be rejected, since the catheter employed cannot be used in medico-technical equipment from other suppliers, which nowadays is a condition for efficient health care. Moreover, one has not been able to cope with the problem of blood, adhering to the needle, dripping from it and through said opening in the short side of the sheath or the slot therein, which obviously exposes the medical personnel using the device to the risk of infection.

Another major drawback is that most of the prior-art solutions are complex, involving a complicated design which entails comparatively high production costs.

SUMMARY OF THE INVENTION

A first aim of the present invention is to provide a device for protecting a needle both before and after use, which is automatically operated in normal handling in connection with the withdrawal of the needle after a catheter has been placed in a blood vessel or in the tissue of a patient.

A second aim of the invention is to provide a device which in an initial phase is equally easy to use as the prior-art devices, in respect of operation and force exertion.

A third aim of the invention is to provide a device which ensures high safety against unintentional or intentional exposure of primarily the needle point after use of the device and activation of the protective means.

A fourth aim of the invention is to provide a device which has a means for absorbing fluid adhering to the needle.

A fifth aim of the invention is to provide a device which prevents the outflow of blood or leakage from the catheter housing, after the needle has been used and retracted to its final position and, until other medico-technical equipment is to be connected to the catheter housing.

Also, the device according to the invention should be usable in infusion cannula embodiments of different types, and have a simple and cost-effective design.

According to the present invention a device for protecting a needle in medico-technical equipment, both before and after use of such equipment, comprises an elongate tubular sheath having an anterior and a posterior end a pointed needle arranged in said sheath for displacement between a first, retracted end position and a second, extended end position, a catheter initially supported by the needle, and an attachment for displacing the needle between said first and said second end positions, and characterised in that a sealing means for sealing the anterior, initially open end of the sheath is detachably connected to said attachment, that said sealing means further is detachably connected to said catheter, that said sealing means during displacement of the needle from said first, retracted end position to said second, extended end position is moved in a direction towards the anterior end of the sheath to a sealing position, and that said sealing means is fixed in said sealing position for substantial sealing of the anterior end of the sheath.

BRIEF DESCRIPTION OF THE DRAWINGS

Embodiments of the invention will be described by way of example, reference being made to the Figures of the accompanying diagrammatic drawings in which.

DESCRIPTION OF THE PREFERRED EMBODIMENT

FIGS. 1–6 illustrate an embodiment of a protective device which is arranged in a schematically illustrated infusion cannula 2. The infusion cannula 2 consists essentially of an elongate, tubular sheath 4 having an anterior, initially open end 6 and a posterior, open or closed end 8. The sheath 4 is provided with at least one slot 10 which is extended in the longitudinal direction of the infusion cannula 2 and which has a region of reduced slot width 14 in the vicinity of a posterior end of the slot 10. The purpose of this region of reduced slot width 14 will be explained below.

Inside the infusion cannula 2, there is provided an attachment 16 for a needle 18 having a sharp point 20. The attachment 16 (see FIG. 2) has in the embodiment here illustrated, two wings 22 which by a respective web portion 24 are connected to the attachment 16 proper. As appears especially from FIG. 2, each web portion 24 extends through a slot 10 in the sheath 4, such that the wings 22 are located on the outside of the sheath 4 while the attachment 16 is located inside the sheath 4. The web portion 24 has a height adapted to the normal width of the slot 10. In this manner, it is possible to displace the attachment 16 and the needle 18 mounted thereon in the longitudinal direction of the infusion cannula 2 along the slots 10 in the sheath 4.

Figure 5:
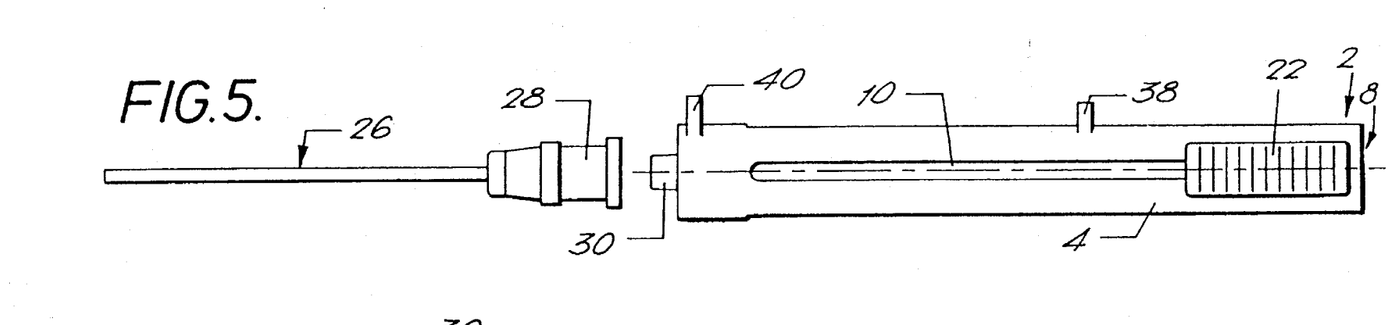
FIG. 5 is a side view of the infusion cannula after separation from a catheter initially supported by the needle of the infusion cannula.
Figure 6:
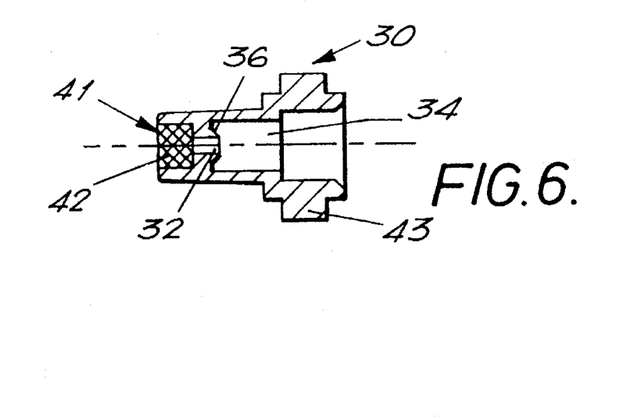
FIG. 6 is cross-section of a sealing means.

The needle 18 supports a catheter 26 having a catheter housing 28 (see especially FIG. 5), which is detachably connected to a sealing means 30 which is supported by the needle 18 and the attachment 16 in a position between the catheter housing 28 and the attachment 16, and which is provided for substantially sealing the anterior, initially open end 6. As seen in FIG. 6, there is provided a passageway 32 which extends through the sealing means 30 coaxially with the longitudinal axis of the needle 18. The passageway 32 preferably has a circular cross-sectional profile with an inner diameter which is equal to or slightly larger than the outer diameter of the needle 18.

In the end of the sealing means 30 facing away from the point 20 of the needle, there is provided a chamber or recess 34, and in the opposite, anterior end of the sealing means 30 there is provided a recess 41. In the region of the mouth of the passageway 32 in the bottom of the recess 34, there is a conical, raised portion 36, whose function will be explained below. The outer dimensions of the sealing means 30 are adapted to the inner dimensions of the sheath 4. In the illustrated embodiment, the sealing means 30 has a circular cross-section which is conformed to the interior shape of the sheath 4 and has a diameter which is equal to or slightly smaller than the diameter of the interior central region of the sheath. It should however be pointed out that the sheath and the sealing means may have another, e.g. hexagonal cross-section.

Figure 1:
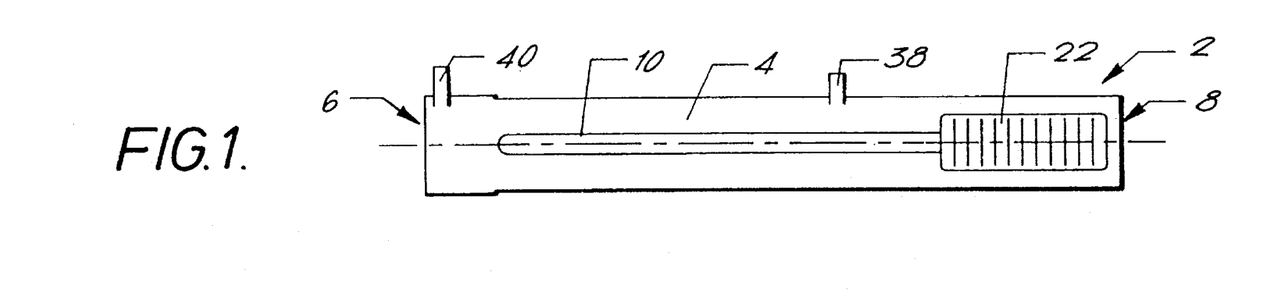
FIG. 1 is a side view schematically illustrating an infusion cannula in a ready-for-use position.
Figure 2:
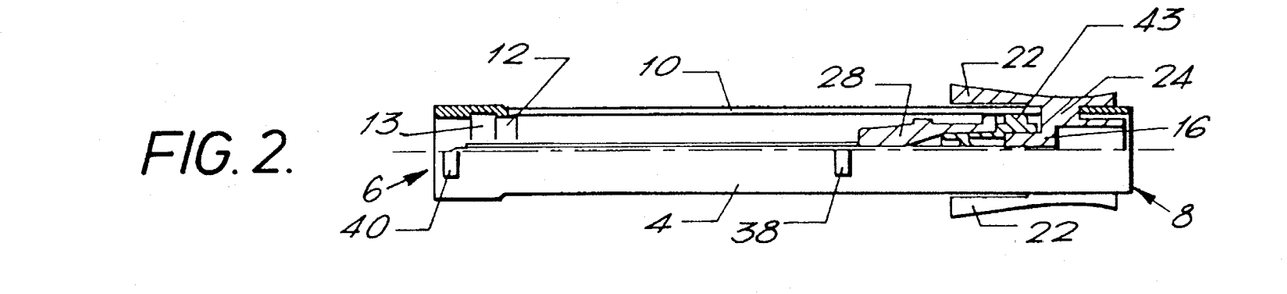
FIG. 2 is a part-sectional top view of the infusion cannula schematically illustrated in FIG. 1 in a ready-for-use position.
Figure 3:
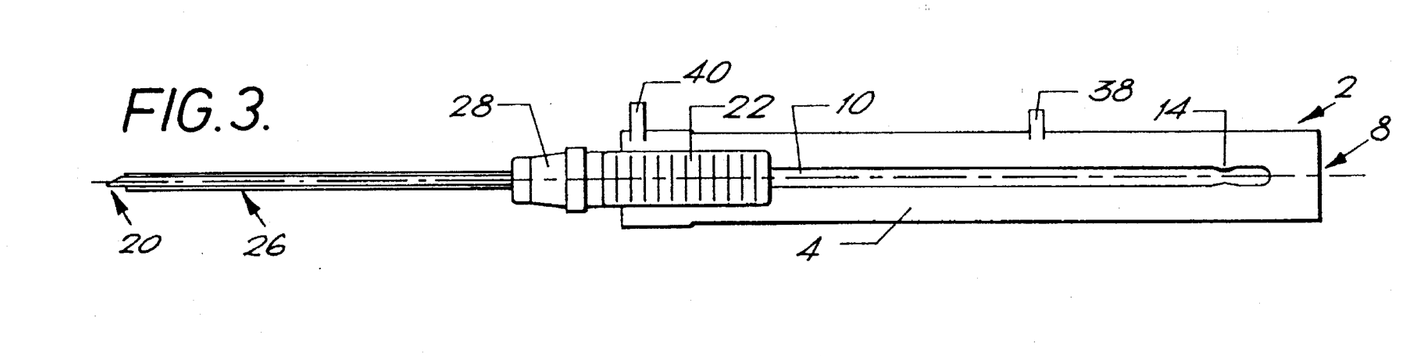
FIG. 3 is a side view of the infusion cannula in a penetrating position.

In the ready-for-use position shown in FIGS. 1 and 2, the attachment 16 is situated in the immediate vicinity of the posterior end 8 of the sheath 4. The web portions 24 are then located on the side of the region 14 of reduced slot width adjacent the posterior end 8 and the needle 18 and the catheter 26 supported thereby are protected within the sheath 4. To displace the needle 18 and the catheter 26 from the ready-for-use position to a penetrating position shown in FIG. 3, a pushing force is applied to the wings 22. To this end, there are provided on the outside of the sheath 4 lugs 38, 40 which serve as gripping abutments. Initially, the region 14 of reduced slot width must be passed, which requires an increased pushing force. Once this region 14 has been passed, the attachment 16 supporting the needle slides without any major force exertion towards the anterior, initially open end of the sheath 4.

When the attachment 16 approaches the final penetrating position, lugs 43 on the sealing means 30 will slide through a local reduced diameter region 12, for instance in the form of sloping plane, into engagement with a recess 13 with an audible click, the recess 13 having a diameter which is equal to or slightly larger than the inner diameter of the sheath 4 in the case of a circular cross-section. This is done without the exertion of any appreciably increased pushing force. Once the region 12 has been passed, the sealing means 30, which is supported by the attachment 16 and through which the needle 18 extends, is thus immovably fixed in the anterior part of the sheath 4, which then is substantially sealed. The device has thus reached the penetrating position of FIG. 3. In this position, the catheter housing 28 is supported by the sealing means 30, which in turn is supported by the attachment 16, to which are connected the two wings 22 providing gripping surfaces for the operator's thumb and middle finger.

Figure 4:
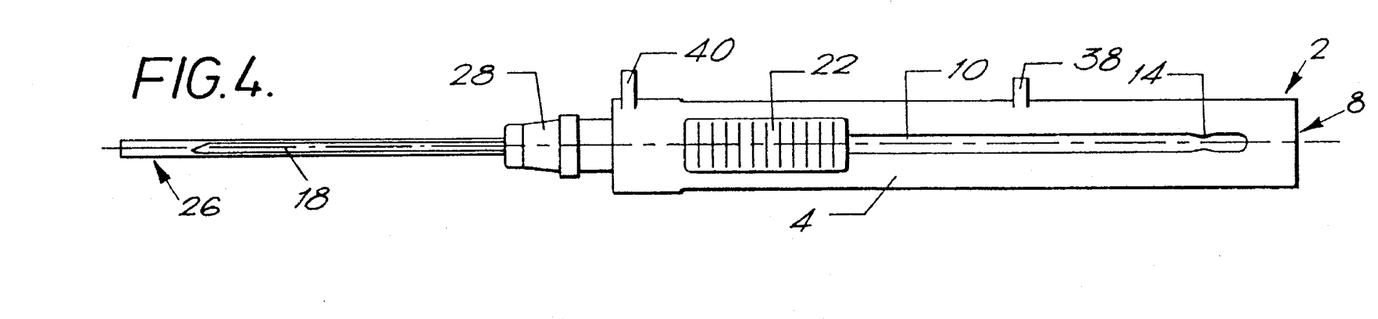
FIG. 4 is a side view of the infusion cannula immediately after the withdrawal of the needle has commenced.

To retract the needle 18 and the rest of the device, the movement described above is reversed, the lugs 38, 40 serving as abutments for e.g. the index finger. The attachment 16 slides, without any major force exertion, back to the posterior region 14 of reduced slot width. During the rearward movement of the attachment 16, the catheter 26 tends, also, to be pulled in a direction towards the anterior end 6 of the sheath 4 as a result of the friction force produced between the outside of the needle 18 and the inside of the catheter 26, whereupon the needle 18 is withdrawn from the catheter, the detachable, fluid tight connection between the catheter housing 28 and the sealing means 30 precluding leakage of fluid, such as blood. By applying an increased force, the posterior region 14 of reduced slot width is traversed, and the needle point 20 is moved into the recess 34 in the sealing means 30.

As mentioned above, the sealing means 30 is immovably fixed in the anterior end of the sheath 4, and the needle 18 will thus pass through and eventually leave the passageway 32 in the sealing means 30. In this position, it is possible to separate the infusion cannula 2 from the catheter housing 28, which is immediately connected to other medico-technical equipment. By providing a means, such as a plug (described in further detail below), which prevents leakage of fluid, such as blood, the device may be safely left in this position for subsequent connection to other medico-technical equipment.

Thanks to the inventive design of the bottom of the recess 34, i.e. the conical shape of the bottom in the region of the mouth of the passageway 32, in combination with the posterior region 14 of reduced slot width, serving as locking means, it is substantially impossible in practice to move the attachment and the needle supported thereby in a direction towards the now substantially sealed end 6 of the sheath. This is so because the needle point 20 will tend to slide along the sloping side walls of the conical mouth 36 of the passageway, and also because a greater force is required for passing the locking means. Thus, it is substantially impossible to again position the needle in the passageway 32 of the sealing means 30.

To prevent fluid, such as blood, which adheres to the needle 18 after use of the infusion cannula, from dripping through the passageway 32 in the sealing means 30 or the slot 10 of the sheath 4, it is preferred, as appears from FIG. 6, to dispose in said chamber or recess 41 or in the passageway 32 a plug 42 through which the needle initially passes and which swells when contacted with fluid, such as blood. Suitable plug materials are e.g. cellular plastics with a large number of open cells. In conjunction with the retraction of the needle 18, this will thus be wiped against the plug 42. Fluid, such as blood, adhering to the needle 18 will be absorbed by the plug 42, which starts swelling so as to finally seal the passageway 32 when the needle has been completely retracted. As a result, the needle will be essentially free from adhering fluid, and there is thus no risk of fluid dripping. The plug 42 also precludes leakage of fluid through the passageway 32, such that the catheter housing can be fixed on the patient in peace and quiet, before the infusion cannula is separated from the catheter housing 28, which in turn is connected to other equipment.

There is thus provided an infusion cannula in which the needle is protected by an enclosing sheath both before and after the use of the infusion cannula. The protective device is automatically activated in connection with normal handling of the equipment, i.e. when the needle is withdrawn from the patient's vein or tissue.

The compact design permits handling the infusion cannula with only one hand, which is preferred in medical care. By the small external dimensions, a very acute angle is had between the patient's skin and the needle, which is an advantage when the catheter is to be placed on the patient.

The combination of a sealing means which essentially prevents displacement of the needle out of its protected end position after use of the infusion cannula, and the configuration of the mouth region of the passageway on the side of the sealing means facing away from the anterior end provides high safety against intentional or unintentional exposure of the needle after the infusion cannula has been used.

The provision of a plug which swells or expands upon contact with fluid not only ensures complete sealing of the anterior, initially open end of the infusion cannula, but also prevents blood that may adhere to the needle from dripping through the passageway in the sealing means or through the slot in the sheath.

Figure 7:
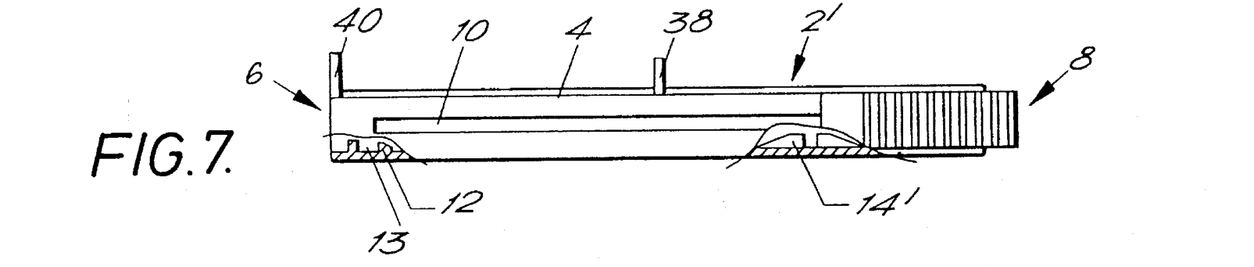
FIG. 7 is a part-sectional view schematically illustrating a preferred embodiment of the infusion cannula in a ready-for-use position.
Figure 8:
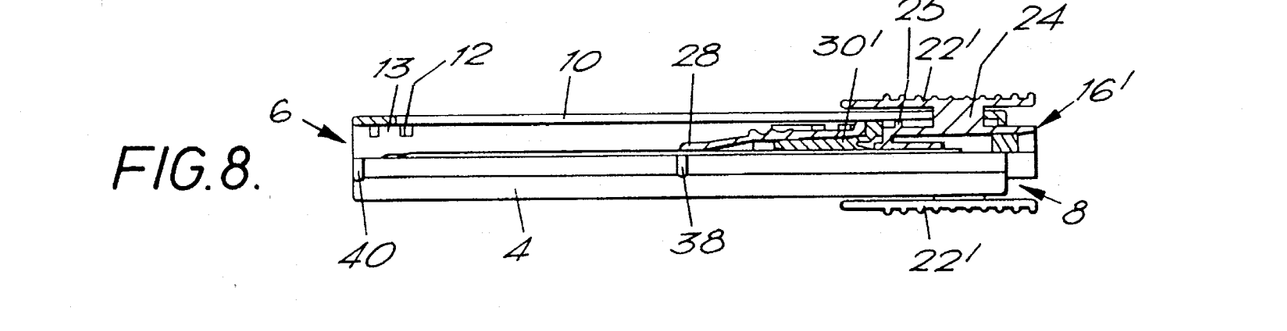
FIG. 8 is a part-sectional top view of the infusion cannula schematically illustrated in FIG. 7 in a ready-for-use position.
Figure 9:
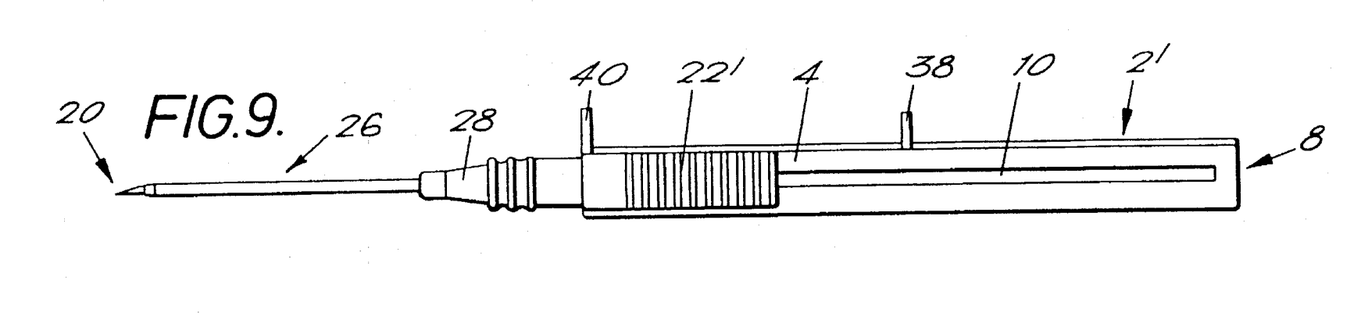
FIG. 9 is a side view of the preferred infusion cannula in a penetrating position.

FIGS. 7–13 illustrate a preferred embodiment of a protective device which is arranged in a schematically illustrated infusion cannula 2'. The infusion cannula 2' consists essentially of an elongate, tubular sheath 4 having an anterior, initially open end 6 and a posterior, open or closed end 8. The sheath 4 is provided with at least one slot 10 which extends in the longitudinal direction of the infusion cannula 2'. Within the sheath 4 adjacent the end 8 there is provided lockings means in the form of opposed projections 14' which between them define a gap 15' (FIG. 13) which cooperates with one or more projections 25 provided on an attachment 16' as will be explained. The projections 25 in the ready-to-use position of the cannula shown in FIGS. 7 and 8, are located behind, that is on the posterior side of the projections 14'.

Inside the infusion cannula 2', there is provided the attachment 16' for supporting a needle 18 having a sharp point 20. The attachment 16' (see FIG. 8) has in the preferred embodiment here illustrated, two wings 22' which by a respective web portion 24 are connected to the attachment 16' proper. As appears especially from FIG. 8, each web portion 24 extends through a slot 10 in the sheath 4, such that the wings 22' are located on the outside of the sheath 4 while the attachment 16' is located inside the sheath 4. The web portion 24 has a height adapted to the normal width of the slot 10. In this manner, it is possible to displace the attachment 16' and the needle 18 mounted therein in the longitudinal direction of the infusion cannula 2' along the slots 10 in the sheath 4. Clearly, initially extra effort is required to force the projections 25 past the projections 14'. Either or both the projections 25 and the projections 14' are resilient.

Figure 11:
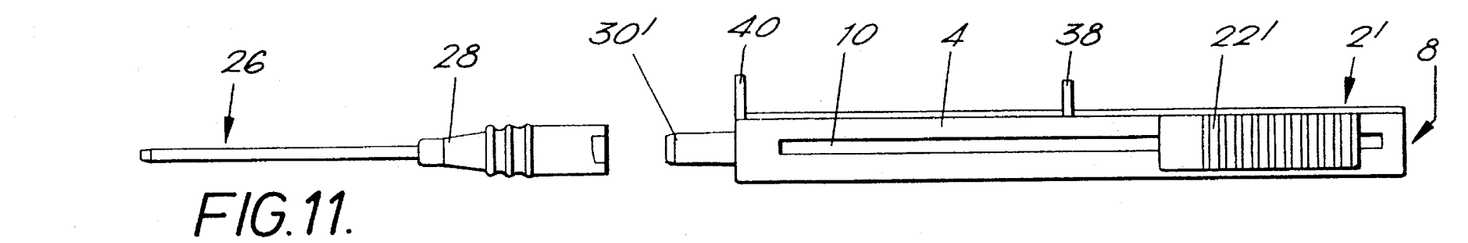
FIG. 11 is a side view of the preferred infusion cannula after separation from a catheter initially supported by the needle of the infusion cannula.
Figure 12:
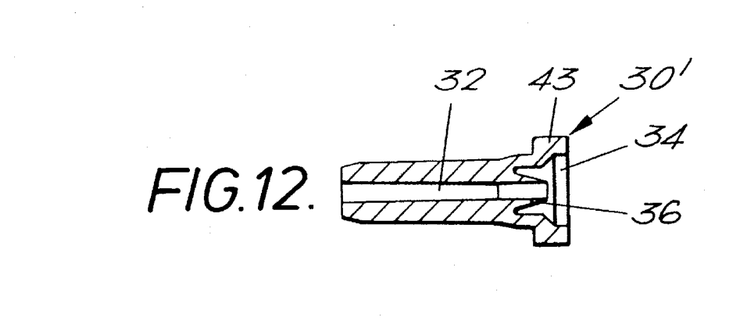
FIG. 12 is cross-section of a sealing means of the infusion cannula schematically illustrated in FIGS. 7 to 11.

The needle 18 supports a catheter 26 having a catheter housing 28 (see especially FIG. 11), which is detachably connected to a sealing means 30' which is supported by the needle 18 and the attachment 16' in a position between the catheter housing 28 and the attachment 16', and which is provided for substantially sealing the anterior, initially open end 6. As seen in FIG. 12, there is provided a passageway 32 which extends through the sealing means 30' coaxially with the longitudinal axis of the needle 18. The passageway 32 preferably has a circular cross-sectional profile with an inner diameter which, in at least a portion, is equal to the outer diameter of the needle 18, when assembled. That means that said inner diameter initially may be slightly smaller than the outer diameter of said needle 18.

In the end of the sealing means 30' facing away from the point 20 of the needle, there is provided a recess 34 for connection with the attachment 16'. In the region of the mouth of the passageway 32 in the bottom of the recess 34, there is a conical, raised portion 36. The outer dimensions of the sealing means 30' are adapted to the inner dimensions of the sheath 4. In the illustrated embodiment, the sealing means 30' has a essentially circular cross-section which is conformed to the interior shape of the sheath 4 and has a diameter which is equal to or slightly smaller than the diameter of the interior central region of the sheath. It should however be pointed out that the sheath and the sealing means may have another, e.g. hexagonal cross-section.

Figure 13:
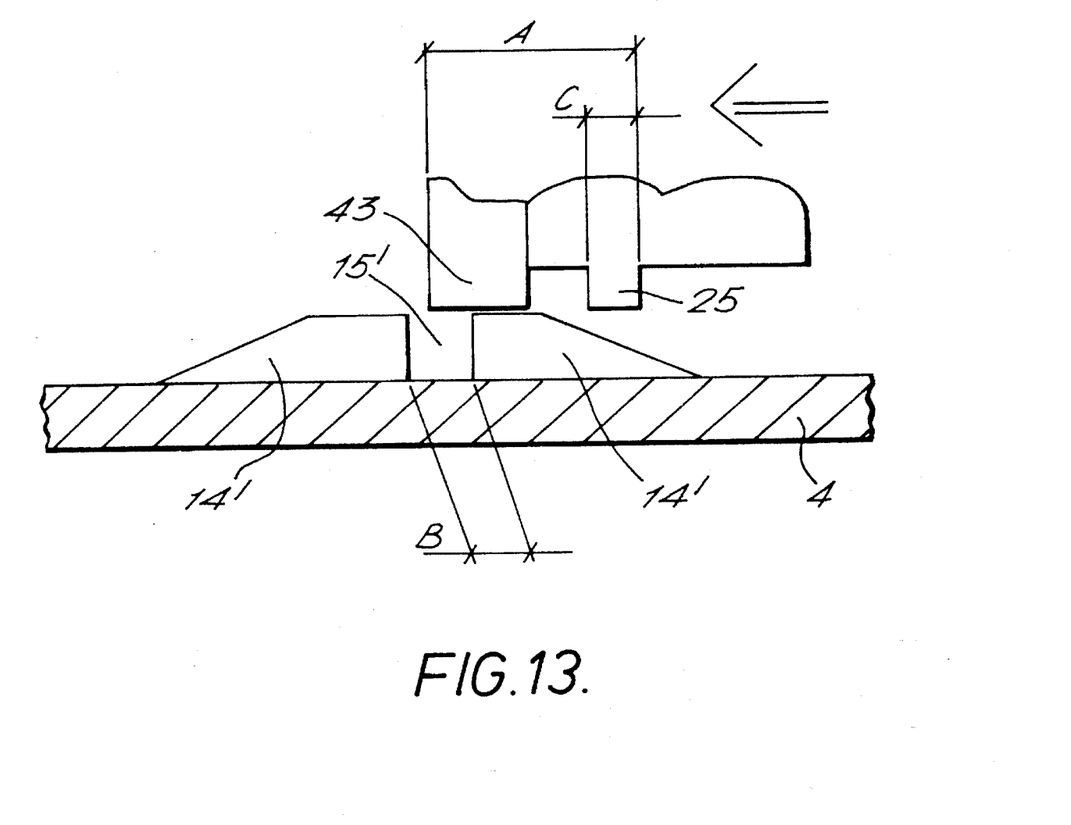
FIG. 13 is a detail of a locking means forming part of the infusion cannula of FIGS. 7 to 11.

In the ready-for-use position shown in FIGS. 7 and 8, the attachment 16' is situated in the immediate vicinity of the posterior end 8 of the sheath 4. The web portions 24 are then located adjacent the posterior end 8, and the needle 18 and the catheter 26 supported thereby are protected within the sheath 4. To displace the needle 18 and the catheter 26 from the ready-for-use position to a penetrating position shown in FIG. 9, a pushing force is applied to the wings 22'. To this end, there are provided on the outside of the sheath 4 lugs 38, 40 which serve as gripping abutments. Initially, the projections 25 interconnected with the attachment 16' must be passed, clear of the projections 14' which requires an increased pushing force. At this time, the sealing means 30' is detachably connected to the attachment 16' and as is illustrated in FIG. 13 the dimension 'A' is greater than the dimension 'B', that is the width of the gap 15' so that the projections 25 pass over the projections 14'. Once the projections 25 are clear of said projections 14', the attachment 16' supporting the needle slides without any major force exertion towards the anterior, initially open end 6 of the sheath 4.

When the attachment 16' approaches the final penetrating position, lugs 43 on the sealing means 30' will slide through a local projection 12, for instance in the form of sloping plane, into engagement with a recess 13 thus making an audible click. This is done without the exertion of any appreciably increased pushing force. Once the projection 12 has been passed, the sealing means 30', which is supported by the attachment 16' and through which the needle 18 extends, is thus immovably fixed in the anterior part of the sheath 4, which then is substantially sealed. The device has thus reached the penetrating position of FIG. 9. In this position, the catheter housing 28 is supported by the sealing means 30', which in turn is supported by the attachment 16', to which are connected the two wings 22' providing gripping surfaces for the operator's thumb and middle finger.

Figure 10:
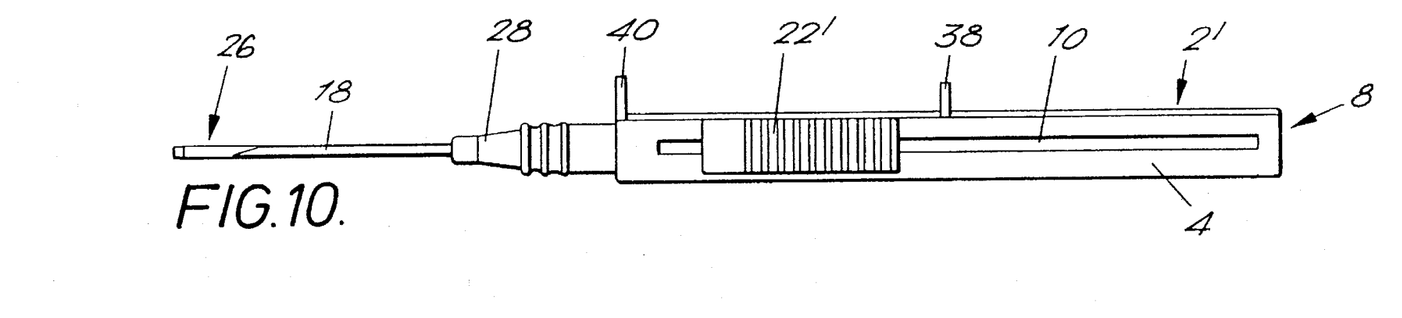
FIG. 10 is a side view of the infusion cannula illustrated in FIG. 9 immediately after the withdrawal of the needle has commenced.

To retract the needle 18, the movement described above is reversed, the lugs 38, 40 serving as abutments for e.g. the index fingers. The attachment 16' slides, without any major force exertion, back to the posterior end 8. During the rearward movement of the attachment 16', the catheter 26 tends, also, to be pulled in a direction towards the anterior end 6 of the sheath 4 as a result of the friction force produced between the outside of the needle 18 and the inside of the catheter 26, whereupon the needle 18 is withdrawn from the catheter, the detachable, fluid tight connection between the catheter housing 28 and the sealing means 30' precluding leakage of fluid, such as blood. By applying an increased force, said locking means 14' is traversed, and the needle point 20 is moved into the passageway 32 in the sealing means 30'. As mentioned above, the sealing means 30' is immovably fixed in the anterior end of the sheath 4, and the point 20 of the needle 18 will thus come to a halt within the passageway 32 in the sealing means 30'. In this position, it is possible to separate the infusion cannula 2' from the catheter housing 28, which is immediately connected to other medico-technical equipment.

Thanks to the design of the passageway 32, in combination with the projections 25 and locking means 14' it is impossible in practice to move the attachment and the needle supported thereby in a direction towards the now substantially sealed end 6 of the sheath. This is so because the attachment 16' is fixed in its final position by the projections 25 which are now located in the gap 15' defined by projections 14'. The dimension 'C' of the projections 25 being less than the dimension 'B' of the gap 15' (see FIG. 13).

To seal the passageway 32, the needle 18 is situated within said passageway 32, the diameter of which is equal in at least a portion to the diameter of the needle 18. In practice the passageway 32 and more exactly the conical, raised portion 36 is formed with a diameter which is slightly smaller than tile diameter of the needle 18. Since the material used has some flexibility, it is possible to press the needle 18 into the passageway 32, when assembling the device. Thereafter the material will relax and thus the passageway 32 will have a diameter essentially equal to the diameter of the needle 18. Therefore, the device is liquid-tight until the infusion cannula 2', i.e. the means 30', is separated from the catheter housing 28.

There is thus provided an infusion cannula in which the needle is protected by an enclosing sheath both before and after the use of the infusion cannula. The protective device is automatically activated in connection with normal handling of the equipment, i.e. when the needle is withdrawn from the patient's vein or tissue.

The compact design permits handling the infusion cannula with only one hand, which is preferred in medical care. By the small external dimensions, a very acute angle is had between the patient's skin and the needle, which is an advantage when the catheter is to be placed on the patient.

The combination of a locking means which essentially prevents displacement of the needle out of its protected end position within the passageway of the sealing means after use of the infusion cannula, and the configuration of the sealing means itself provides high safety against intentional or unintentional exposure of the needlepoint after the infusion cannula has been used.

The provision of these means ensures complete sealing of the anterior, initially open end of the infusion cannula.

Modifications can be made to the embodiments herein described. For example, only one slot may be provided in the sheath of the infusion cannula. The slot or slots may also be of a different design. The region of reduced slot width and the projections and recesses may be replaced with other types of locking mechanisms. Thus, it is conceivable to provide recesses which are extended transversely of the longitudinal direction of the slot, such that the web portion between the attachment and the operating member snap into these recesses. The plug described above for sealing the passageway of the sealing means may alternatively consist of rubber of a combination of rubber and a felt material, which expands after the needle has been retracted so as to seal the passageway.

I claim:

1. A device for protecting a needle in medico-technical equipment, both before and after use of such equipment, comprising an elongate tubular sheath (4) having a normally open anterior end (6) and a posterior end (8), said sheath having at least one slot extending in the longitudinal direction of said sheath, a pointed needle (18) arranged in said sheath (4) between a first, retracted end position where said needle is enclosed within said sheath and a second, extended end position where said needle extends outwardly through said normally open anterior end, a catheter (26) initially supported by the needle (18) in said first position, said catheter having a hub, and an attachment (16, 16') affixed to said needle, said attachment having a wing extending outwardly through said at least one slot in said sheath for manually displacing the needle (18) between said first and said second end positions, a sealing means (30, 30') located intermediate said attachment means and said hub of said catheter and detachably connected to said attachment (16, 16') and said catheter hub is detachably connected to said sealing means, said needle being movable between said first position to said second position by manipulation of said attachment by a user, whereby said sealing means (30, 30') during displacement of the needle (18) from said first, retracted end position to said second, extended end position is moved within said sheath in a direction towards the anterior end (6) of the sheath (4) and seats in a position sealing the normally open anterior end of said sheath, and means to fix said sealing means in said sealing position for substantial sealing of the anterior end (6) of the sheath (4), said catheter hub adapted to be manually detached from said sealing means in said sealing position to allow removal of said medico-technical equipment from said catheter.

2. A device as claimed in claim 1, characterized in that said sealing means (30) has a shape and dimensions conformed to the interior of the sheath (4), that said sealing means (30) is provided with a passageway (32) having a diameter which is equal to or slightly greater than the outer diameter of the needle (18), and that said means to fix said sealing means in said sealing position comprises at least one lug (43) formed in said sealing means (30) which is intended, in the second, extended position of the needle (18), to be brought into engagement with a recess (13) provided inside the sheath (4) in the immediate vicinity of said anterior end.

3. A device as claimed in claim 2, characterized in that said sealing means has a recess formed therein surrounding said passageway on the side of said sealing means facing away from the anterior end of the sheath having such a shape and such an extent that the point of the needle, after use, will be located in said recess.

4. A device as claimed in claim 3, characterized in that said recess is formed in said sealing means surrounding said passageway (32), on the side facing away from the anterior end (6) of the sheath (4) for detachable connection with the attachment (16').

5. A device as claimed in claim 2, characterized in that the engagement of said at least one lug with the recess is such that an audible click is produced confirming to the user that the end position has been reached.

6. A device as claimed in claim 1 characterized in that said sheath has an inwardly directed projection at its anterior end extending to a depth within the interior of the sheath, said depth increasing in the direction toward the anterior end forming a slope and said sealing means (30) has a shape and dimensions conformed to the interior of the sheath (4), that said sealing means (30) is provided with a passageway (32) having a diameter which is equal to or slightly greater than the outer diameter of the needle (18), and that said sealing means (30) has an annular, resilient flange which is intended, in the second, extended end position of the needle (18), to be passed over said slope of said inwardly directed projection, said annular flange being in a position of engagement beyond the end of said slope.

7. A device as claimed in claim 6, characterized in that an annular recess is formed in the sealing means surrounding said passageway on the side of said sealing means facing away from the anterior end of the sheath having such a shape and such an extent that the point of the needle, after use, will be located in said recess.

8. A device as claimed in claim 7, characterized in that the recess (34) has such a shape as to prevent re-entry of the needle (18) into the passageway (32), once the needle point (20) has been withdrawn from the passageway in moving the needle (18) from the second, extended end position to the first, retracted end position.

9. A device as claimed in claim 6, characterized in that the seating of said annular flange in engagement beyond said slope within the interior of the sheath causes an audible click sound confirming to the user that the end position has been reached.

10. A device as claimed in claim 1, characterized in that there is provided at least one locking means (14) for releasably fixing said attachment (16) in said first, retracted end position, and said means to fix said sealing means in said sealing position comprises at least one lug (43) formed in said sealing means (30) which interacts with a recess (13) formed in said sheath for immovably fixing the sealing means in said sealing position.

11. A device as claimed in claim 10, characterised in that said at least one locking means (14) is formed by a local reduction of the width of the slot (10) in the vicinity of said first, retracted end position of the attachment (16), said local reduction of the width of the slot (10) being so designed as to prevent unintentional displacement of the attachment (16), but being traversable in both longitudinal directions by applying a sufficiently high pushing force when displacing the needle (18) between said first, retracted and said second, extended end position, and between said second, extended and said first, retracted end position, respectively.

12. A device as claimed in claim 1, characterized in that there is provided at least one locking means (14') for releasably fixing said attachment for movement from said first, retracted end position to said second, extended position and for immovably fixing said attachment (16') after manually detaching said catheter therefrom, and return of said attachment to said first, retracted position after use of the equipment, and said means to fix said sealing means in said sealing position comprises at least one lug (43) formed in said sealing means (30) adapted to interact with a recess provided inside said sheath (4) for immovably fixing the sealing means (30') in said sealing position.

13. A device as claimed in claim 12, characterized in that said at least one locking means comprises at least one projection (25) formed on the attachment (16') and a plurality of opposed projections (14') formed within said sheath, said plurality of opposed projections forming a a gap (15') between opposed projections (14') on the inside surface of the sheath (4), said at least one projection interacting with said gap so as to prevent unintentional displacement of the attachment (16') after use of the equipment.

14. A device as claimed in claim 1, characterized in that the sealing means (30) is provided with a passageway (32) having a diameter which is equal to or slightly greater than the outer diameter of the needle (18) and further has a recess formed therein on the side of said sealing means facing the anterior end (6) of the sheath (4), a plug (42) positioned within said recess, said plug comprised of a material that expands when contacted with a fluid for complete, fluid tight sealing of the passageway and thus of the anterior end of the sheath after the needle has been used.

15. A device as claimed in claim 1, characterized in that there is provided on the outside of the sheath (4) at least one lug (38, 40) serving as an abutment when displacing the needle (18) between said first, retracted end position and said second, extended end position.

16. A device as claimed in claim 1, characterized in that the sealing means (30, 30') has a such a shape as to be detachably connectable to a catheter housing (28) of standard design for this type of medical equipment, and that this connection is completely fluid tight until it has been intentionally undone.

* * * * *